United States Patent [19]

Redziniak et al.

[11] Patent Number: 4,621,023
[45] Date of Patent: Nov. 4, 1986

[54] METHOD OF HOMOGENIZING DISPERSIONS OF HYDRATED LIPIDIC LAMELLAR PHASES AND SUSPENSIONS OBTAINED BY THE SAID METHOD

[75] Inventors: Gérard Redziniak, Sartrouville; Alain Meybeck, Courbevoie, both of France

[73] Assignee: Parfums Christian Dior, France

[21] Appl. No.: 541,426

[22] Filed: Oct. 13, 1983

[30] Foreign Application Priority Data

Oct. 15, 1982 [FR] France .................. 82 17311

[51] Int. Cl.⁴ .................. B05D 1/36
[52] U.S. Cl. .................. 428/402.2; 252/312; 252/314
[58] Field of Search .................. 428/402.2; 252/312, 252/314

[56] References Cited

U.S. PATENT DOCUMENTS 4,016,100  4/1977  Suzuki .................. 427/3

FOREIGN PATENT DOCUMENTS 4223  9/1979  European Pat. Off. .
36676  9/1981  European Pat. Off. .
366518  2/1963  Switzerland .

OTHER PUBLICATIONS

Emulsions: Theory Practice, Paul Becher, Reinhold Publishing Corporation, New York, pp. 227–239.

Primary Examiner—Amelia B. Yarbrough
Attorney, Agent, or Firm—Steinberg & Raskin

[57] ABSTRACT

The invention concerns a method of homogenizing dispersions of hydrated lipidic lamellar phases and suspensions obtained thereby which can be applied particularly to the making of products intended for cosmetic, pharmaceutical and medical uses.

The method consists in dispersing in a dispersion liquid a lipidic phase or a lipidic lamellar phase containing one or several amphiphilic lipids and then in homogenizing the said dispersion by feeding the same under a pressure comprised between 10,000 and 70,000 kPa into a passageway of small width defined between the walls of an orifice and the edges of an obturating element arranged in the section of the orifice adjustably, against the flow of the dispersion.

29 Claims, 4 Drawing Figures

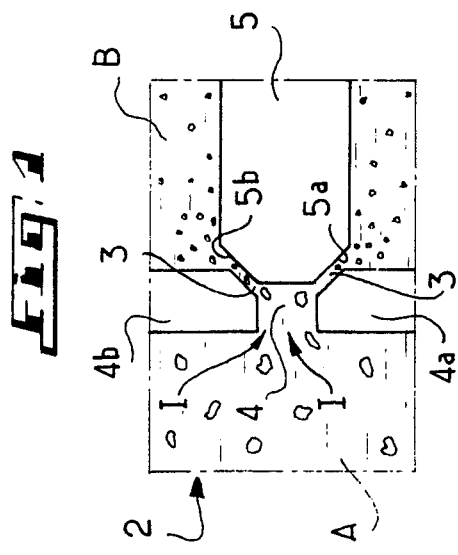
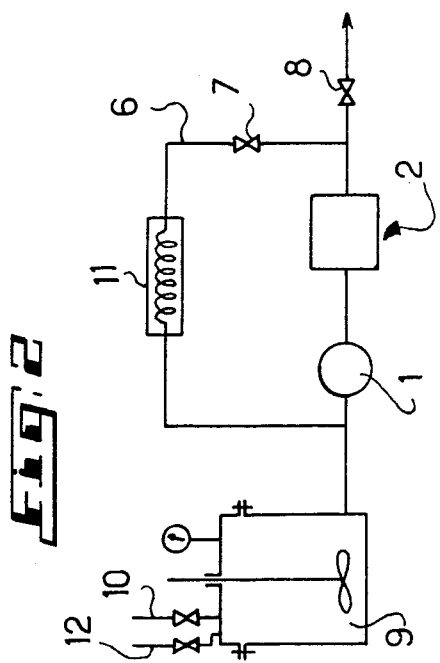
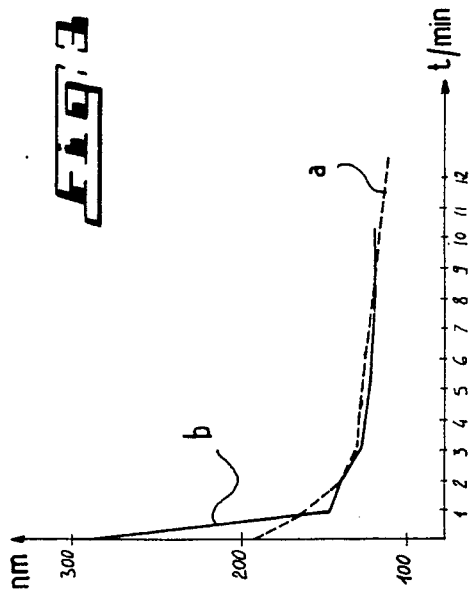
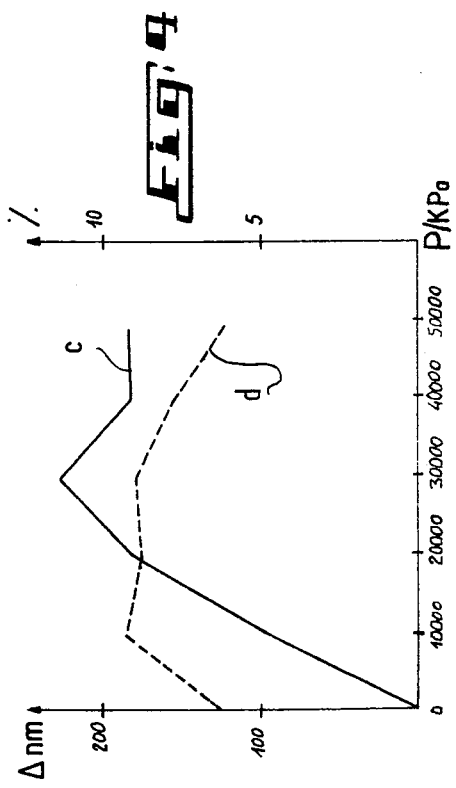

METHOD OF HOMOGENIZING DISPERSIONS OF HYDRATED LIPIDIC LAMELLAR PHASES AND SUSPENSIONS OBTAINED BY THE SAID METHOD

BACKGROUND OF THE INVENTION

The present invention relates to a method of homogenizing dispersions of hydrated lipidic lamellar phases such as, for example, liposomes, and has more particularly as a subject matter a method of homogenizing such a dispersion under pressure.

There are already known several methods such as, for example, dialysis, sonication, mechanical processes which allow homogenizing a suspension of hydrated lamellar phases so as to obtain a relatively homogeneous suspension of lamellar phases such as liposomes. However, these methods allow treating during each operation only a small amount of suspension and, therefore, are not easy to utilize for the production of suspensions of liposomes on an industrial scale.

SUMMARY OF THE INVENTION

The present invention has as its purpose to remedy all the above drawbacks by providing a new method of homogenizing a dispersion of hydrated lipidic lamellar phases, which allows homogenizing a volume of hydrated lipidic lamellar phase suspension suitable from the point of view of industrial production. Moreover, the quality of the homogenization thus performed allows avoiding the addition of emulsifiers and the use of preservatives, since the homogeneous suspension may undergo for example a sterilizing filtration. It also allows obtaining, quite unexpectedly, a very high rate of encapsulation in the said lamellar phases, of substances which possibly are present in the aqueous phase of the said suspension.

To this end, the present invention has as a subject matter a method of obtaining a homogenized suspension of hydrated lipidic lamellar phases in a liquid, such as for example liposomes, consisting in dispersing in the said liquid a lipidic phase or a lipidic lamellar phase containing one or several amphiphilic lipids such as, for example, lecithin or the like, and then in homogenizing the said dispersion by feeding the latter, under pressure, into a passageway of small width defined between the walls of an orifice and the edges of an obturating element adjustably arranged in the section of the said orifice, against the flow of said dispersion, characterized in that the feeding pressure is comprised between about 10,000 kPa and about 70,000 kPa.

According to another feature of said method, there are performed several successive passages of the dispersion through the said passageway. Advantageously, the pressure under which the dispersion is fed into the said passageway is comprised between about 10,000 kPa and about 40,000 kPa and is preferably of the order of about 30,000 kPa.

Advantageously, when the dispersion is recycled into the said passageway, the said dispersion is cooled every time before it is fed into the said passageway.

Furthermore, according to one advantageous form of embodiment of the invention, the said dispersion contains from 50% to 99.9% approximately of liquid and from 0.1 to 50% of the said lipidic phase containing one or several amphiphilic lipids such as for example lecithin or the like, or from 20 to 99.9% of liquid and from 80 to 0.1% of the said hydrated lipidic lamellar phase.

The said liquid is preferably an aqueous physiological solution of sodium chloride or of d-glucose, the liquid being, if appropriate, a solution of an active product to be encapsulated in the lipidic phase.

According to another feature of the method of the invention, the suspension to be homogenized is fed under pressure in an inert atmosphere.

The invention also has as a subject matter a suspension of hydrated lipidic lamellar phases obtained by the above-described method, the size of the particles of which is comprised between 30 and 150 nanometers, and, on an average, is about 100 nanometers, these sizes have been evaluated by means of electron microscopy and their average by means of an apparatus called a nano-sizer.

Advantageously, this suspension is sterilized by way of sterilizing filtration, preferably at room temperature. Thus, it is not necessary to add to the homogenized suspension obtained by the method of the invention, preserving additives which often are undesirable in products intended for pharmaceutical or cosmetic uses.

BRIEF DESCRIPTION OF THE DRAWINGS

The invention will be better understood and other features, details and advantages of the latter will appear more clearly as the following explanatory description proceeds with reference to the appended diagrammatic drawings given solely by way of example and wherein:

FIG. 1 is a diagrammatic view illustrating the principle of the homogenizing method of the invention;

FIG. 2 is a block diagram illustrating an installation for the production of a homogenized suspension by the method of the invention;

FIG. 3 is a graph illustrating the variation in size of the particles contained in the suspension with the duration of the homogenizing treatment; and FIG. 4 is a graph in which the curve c shows the variation in size difference between the particles, before the homogenizing treatment and after the homogenizing treatment, with the feeding pressure of the suspension, whereas curve d shows the variation in the rate of encapsulation of the active product in the hydrated lipidic lamellar phase with the homogenizing pressure.

DESCRIPTION OF THE PREFERRED EMBODIMENTS

Referring to FIGS. 1 and 2, the method of the invention for obtaining homogenized suspensions of hydrated lipidic lamellar phases in a liquid, such as for example a suspension of liposomes, consists in first dispersing a lipidic phase or a lipidic lamellar phase containing one or several amphiphilic lipids such as for example lecithin in the liquid to obtain a dispersion of large particles presented conventionally by phase A of FIG. 1.

The liquid is preferably a physiological aqueous solution of sodium chloride in which, if appropriate, is dissolved a biologically active product and/or a product having organoleptic and/or physiocochemical properties.

Furthermore, the lipidic phase which may contain one or several amphiphilic lipids selected for example from the compounds pertaining to the series of glycolipids, phospholipids or phosphoaminolipids, such as for example soya lecithin or egg lecithin, may also contain compounds of a hydrophobic character such as for example cholesterol, ubiquinone or the like.

This lipidic phase may be obtained by any process capable of providing lamellar phases, e.g. by the atomization process described in U.S. Pat. No. 4,508,703.

Furthermore, the lipidic lamellar phase dispersed in the liquid may be a strongly hydrated lipidic lamellar phase or a weakly hydrated lipidic lamellar phase as will be illustrated in the examples hereinafter, in which, if appropriate, has been encapsulated a biologically active product and/or a product possessing organoleptic and/or physicochemical properties.

The dispersion thus obtained is fed under pressure, by means of a pump 1, into an apparatus 2 the principle of which is illustrated in FIG. 1 and which comprises a passageway 3 of small width defined between the walls 4a, 4b of an orifice 4 and the edges 5a,5b of an obturating element 5 which is adjustably arranged in the section of the orifice 4, against the flow of the dispersion A represented by the arrow I. Under the action of the pressure and the turbulence caused by the small dimensions of the passageway 3, the particles contained in the suspension are reduced into fine particles of the order of from a few ten nanometers to a few hundred nanometers in size.

In the preferred form of embodiment of the method of the invention applied in the installation illustrated in FIG. 2, the dispersion is performed in a dispersion tank 9 by means of, for example, mechanical stirring, the dispersion A thus obtained is sucked by the pump 1 and then introduced under pressure into the apparatus 2. At the outlet of the apparatus, the homogenized suspension B obtained is either drawn off for use, or is partially or totally recycled upstream of the pump 1 for a further passage in the apparatus 2 through the conduit 6 and by means of valves 7, 8. Advantageously, to prevent a heating of the suspension by such successive compressions and passages in the apparatus 2, the suspension B recycled is cooled by means of a cooler 11.

Advantageously, the feeding of the suspension A into the pump 1 may be effected under pressure from a feeding tank referred to as a pre-feeding tank which may be constituted either by the dispersion vat 9 or by any other container arranged between the dispersion vat 9 and the pump 1. In the example illustrated, it will be considered that the dispersion vat 9 also constitutes the tank for pre-feeding under pressure.

To perform this pre-feeding under pressure, the dispersion vat is rendered gas-tight, and a gas under pressure, advantageously an inert gas such as nitrogen, or a rare gas, is supplied above the dispersion A at a pressure comprised between about 100 kPa and 1,000 kPa to preferably obtain a non-oxidizing atmosphere, through the feeding conduit 10. Such pre-feeding under pressure is highly desirable if the dispersion A is of high viscosity, e.g. of the order of from 1,000 to 10,000 centipoise and particularly for homogenizing a suspension of weakly hydrated lipidic lamellar phases with a content of lipidic phase close to about 50%. Furthermore, the feeding of the dispersion liquid and of the lipidic phase in powder form or of the lipidic lamellar phase to be dispersed may be performed for example continuously into the dispersion vat 9 through the conduit 12.

The flow rate at which the treatment according to the method of the invention can be performed is relatively important and depends particularly on the viscosity of the dispersion to be homogenized and on the pressure under which it is fed into the apparatus 2. As an example, under a feeding pressure of 35,000 kPa, the flow rate at which the suspension is treated by the method of the invention is equal to about 57 liters per hour.

The advantages of the method of homogenization under pressure according to the invention will clearly be illustrated by following examples of production of a homogenized suspension of hydrated lipidic lamellar phases. These examples should in no way be considered as limiting the scope of the present invention, since many variations and modifications are possible, especially in the products used.

EXAMPLE 1

(a.) Production of a pulverulent mixture of lipidic constituents by way of atomization 0.3 g of ubiquinone and 120 milliliters of chloroform are added to 20 g of soya lecithin. This mixture is atomized at 75° C. according to the method described in U.S. Pat. No. 4,508,703. After 15 min there are obtained 18 g of a yellow powder with no particular smell, with a yield of 90%.

(b.) Preparation of an aqueous dispersion 10 g of the mixture obtained in stage (a) are added progressively and with stirring to 980 g of a 0.9% aqueous solution of NaCl containing 1% of bovine albumin serum. The stirring is continued for one hour at room temperature in a rotor mixer. The dispersion thus obtained has a milk-yellow appearance.

(c.) Homogenization of the dispersion under pressure

The dispersion obtained in stage (b) hereabove is poured into the feed tank 9 of the installation illustrated in FIG. 2. This dispersion is fed at a pressure of 40,000 kPa and a flow rate of 50 liters per hour.

The dispersion is recycled upstream of the feed pump. The homogenization is continued for 5 minutes and the homogenized suspension obtained has a homogeneous yellow and opalescent appearance.

The table below gives the average size of the particles measured with a nano-sizer as well as the electron microscope observation of the particles of the suspension.

TABLE 1

| Treatment | Size of Dispersed Particles (nm) | Microscope Observations |
|---|---|---|
| Prior to homogenization under pressure | 308 | Liposomes |
| Subsequent to homogenization under pressure | 101 | Liposomes |

This example shows that it is possible to homogenize a dispersion of liposomes with a high flow rate of the solution in apparatus 2. Furthermore, since the method of the invention can be carried out continuously, it is possible to homogenize an important amount of a dispersion of liposomes or of lipidic phases and therefore to produce such a homogenized suspension on an industrial scale. The suspension thus obtained displays properties which are altogether comparable with and even higher than those of the suspension obtained by research laboratory techniques using for example a rotary evaporator and sonication.

EXAMPLE 2

(a) Production of a powder by way of atomization 5 g of soya lecithin solubilized in 25 milliliters of chloroform and 0.05 g of dopamine dissolved in 10 milliliters of methanol are introduced into a 100-ml beaker.

The solution obtained is atomized according to the method of example 1 at 75° C. and a white powder is collected.

(b.) Preparation of a dispersion

The powder collected in (a) is introduced into a 1-l beaker containing 5 g of collagen polypeptides in solution in 500 milliliters of a 0.9% aqueous solution of sodium chloride. The mixture is subjected to magnetic stirring for 2 hours at room temperature.

At the end of the stirring, the average size of the liposomes measured with a nano-sizer is 254 nanometers.

(c.) Homogenization of the dispersion under pressure

The dispersion obtained in (b) is fed into the orifice 3 of the apparatus 2 at a pressure of 40,000 kPa and a flow rate of 50 liters per hour with recycling of the solution upstream of the feed pump. The homogenization is continued for 5 minutes and the average size of the liposomes of the suspension is equal to 98 nanometers.

EXAMPLE 3

10 g of soya lecithin powder obtained by way of atomization according to the method of example 1, 10 g of collagen polypeptides and 920 g of a 0.9% physiological solution of NaCl are introduced into a 2 1-l beaker and are mixed therein for 15 minutes at room temperature by means of a propeller agitator.

The dispersion thus obtained is thereafter sonicated by means of a vibrating-blade sonicator for 1 hour with cooling. As a result of this treatment, the average size of the liposomes is reduced from 300 nanometers to 190 nanometers.

Thereafter, the suspension obtained after the sonication is subjected to a homogenization under pressure according to the method of the invention by feeding the said suspension at a pressure of 35,000 kPa.

The average size of the liposomes is determined for various durations of the homogenization under pressure. The results are represented by the curve a of FIG. 4 obtained by plotting the average sizes of the liposomes as ordinates and the durations of the homogenization as abscissas at 35,000 kPa.

These results show that there are obtained very rapidly particles of an average size of the order of 100 nanometers, which is markedly less than the sizes obtained by the sonication process.

EXAMPLE 4

25 g of soya lecithin powder obtained by atomization according to Example 1, 2.5 g of adenosin triphosphate disodic salt (Na$_2$ATP) and 472.5 g of a 0.9% solution of NaCl are introduced into a 1-l beaker and mixed for 15 minutes at room temperature by means of a propeller agitator. The suspension thus obtained is subjected to the homogenizing method of the invention at a feeding pressure of 40,000 kPa. The size of the liposomes thus obtained is measured for different treatment durations. The results obtained are represented by the curve b of FIG. 3, which shows, as in Example 3, that there are very quickly obtained particles of an average size of about 100 nanometers.

It follows from Examples 3 and 4 that the method of homogenization of the invention allows obtaining a suspension with particles of a very small average size even if the dispersion treated contains particles of relatively large average size.

Moreover, dispersions prepared as in Example 4 are subjected to homogenization under pressure for a specific duration of 5 minutes at different feed pressures. In each suspension obtained, the average size of the particles or liposomes is measured as well as the rate of encapsulation of Na$_2$ATP in such liposomes.

The results obtained are represented by the curves C and D of FIG. 4.

The curve C represents the variation of the average size difference of the liposomes between the size before the homogenization under pressure and the size after a treatment of 5 minutes at various working pressures. The maximum reduction in average size of the particles is obtained at pressures higher than about 20,000 kPa.

The curve d represents the percentage of encapsulation of Na$_2$ATP obtained after 5 minutes of homogenization under pressure of the suspension of liposomes, at various feed pressures. This curve shows that a maximum rate of encapsulation is obtained at feeding pressures comprised between 10,000 kPa and 40,000 kPa approximately.

Moreover, it appears from FIG. 4 that at a pressure of about 30,000 kPa, both the curve c expressing the fineness of the liposomes after the homogenization and the curve d showing the rate of encapsulation obtained pass through a maximum value. This means that, in the method of the invention, it is advantageous to adopt pressures of this order of magnitude.

EXAMPLE 5

(a.) Preparation of a weakly hydrated lipidic lamellar phase

There are poured into the dispersion vat 9 of the installation represented in FIG. 2, 3 kilogrammes of an aqueous solution, e.g. of a physiological solution of NaCl containing a physiologically active product such as aloe extract and 3 kilogrammes of lecithin powder obtained by atomization according to the process of Example 1 which may contain a constituent of a hydrophobic character. There is thus obtained a weakly hydrated lipidic lamellar phase.

(b) Production of the homogenized suspension

To the weakly hydrated lipidic lamellar phase is added a dilution aqueous solution containing for example 0.9% of NaCl or 0.5% of d-glucose to thus obtain a dispersion containing 0.10 to 80% of a weakly hydrated lipidic lamellar phase, and this mixture is thereafter fed into the passageway 3 of the apparatus 2 in order to be homogenized under pressure. The rate of encapsulation of the aloe extract in the liposomes thus produced is comprised between 50 and 70% approximately.

As an alternative, the weakly hydrated lamellar phase may be prepared by dispersing atomized lecithin powder containing, if appropriate, a constituent of hydrophobic character in a smaller amount of an aqueous solution to be encapsulated. There can thus be obtained a weakly hydrated lipidic lamellar phase containing up to 80% of lipidic phase. The mixing is performed for example in a roller mill and is thereafter diluted in a dilution aqueous solution to obtain a dispersion containing from 0.1 to 80% of the said weakly hydrated lipidic lamellar phase as indicated above. The rate of encapsulation of the solution to be encapsulated is also comprised between 50 and 70%.

The above examples show that the homogenizing method of the invention allows obtaining homogenized suspensions of liposomes or of stable, weakly hydrated lipidic lamellar phases. Since the volume of the dispersion treated per unit of time is important and since the method can be carried out continuously, it is possible to produce important amounts of a dispersion of lipidic lamellar phases compatible with production on an industrial scale.

Furthermore, since the size of the liposomes is of the order of about 100 nanometers, it is possible to sterilize these suspensions by way of sterilizing filtration since the size of the microorganisms or bacteria is greater than 220 nanometers.

Thus, the suspension of liposomes can be sterilized in the cold state, which is very important in view of the fact that the compounds constituting the liposomes or encapsulated in the said liposomes are often temperature-degradable. Moreover, since the suspension is sterilized, it is no longer necessary to add preservatives.

Furthermore, since the suspension obtained is very homogeneous, it is generally not necessary to add emulsifiers to stabilize the suspension.

The method of homogenization under pressure according to the invention therefore allows obtaining suspensions of liposomes displaying higher stability and homogeneity than those obtained by dialysis and, above all, allow producing in particular, in a continuous manner and with a satisfactory rate of encapsulation, industrial amounts of dispersions which are absolutely unobtainable by the sonication method of homogenization. Moreover, the homogenization under pressure may be carried out in the cold state without increasing the temperature, whereas the sonication method requires a cooling of the solution to prevent the products constituting the liposomes from degrading.

However, as appears from the decrease in the rate of encapsulation noted in Example 4, the feeding of the dispersion under an excessively high pressure may result in a degradation of the liposomes. Moreover, an excessively high pressure may cause a considerable heating of the solutions (dispersions), which is often harmful.

What is claimed is:

1. A method for obtaining a homogenized suspension of hydrated lipidic lamellar phases entrapping a liquid, comprising the successive steps of:
   (a) providing an appropriate liquid,
   (b) dispersing in said liquid, a lipidic phase or a lipidic lamellar phase containing at least one amphiphilic lipid, thereby obtaining a dispersion of said lipidic phase or lipidic lamellar phase in said liquid, and
   (c) directly feeding said dispersion under a feeding pressure ranging between about 10,000 kPa and about 70,000 kPa into a passageway of small width defined between the walls of an orifice and the edges of an obturating element adjustably arranged in the section of said orifice, against the flow of said dispersion,
   thereby encapsulating said liquid within lipidic lamellar particles of said lipidic lamellar phase by entrapping a part of said liquid within said lipidic lamellar particles and forming a suspension in homogenized form of said encapsulated particles in the remaining liquid, thus achieving a high rate of encapsulation of said liquid within said lipidic lamellar particles.

2. A method for obtaining a homogenized suspension of hydrated lipidic lamellar phases entrapping a liquid, comprising:
   (a) providing an appropriate aqueous liquid,
   (b) dispersing in said aqueous liquid, an appropriate amount of a lipidic phase or a lipidic lamellar phase containing at least one amphiphilic lipid, thereby obtaining a dispersion of said lipidic phase or lipidic lamellar phase in said liquid comprising from 50 to 99.0% of said liquid and from 50 to 0.1% of said lipidic or lipidic lamellar phase, and
   (c) directly feeding said dispersion under a feeding pressure ranging between about 10,000 kPa and about 70,000 kPa into a passageway of small width defined between the walls of an orifice and the edges of an obturating element adjustably arranged in the section of said orifice, against the flow of said dispersion,
   thereby encapsulating said liquid within lipidic lamellar particles of said lipidic lamellar phase by entrapping a part of said liquid within said lipidic lamellar particles and forming a suspension in homogenized form of said encapsulated particles in the remaining liquid, thus achieving a high rate of encapsulation of said liquid within said lipidic lamellar particles.

3. A method for obtaining a homogenized suspension of hydrated lipidic lamellar phases entrapping a liquid, comprising:
   (a) providing an appropriate aqueous liquid,
   (b) dispersing in said liquid, an appropriate amount of a hydrated lipidic lamellar phase containing at least one amphiphilic lipid, thereby obtaining a dispersion of said lipidic lamellar phase in said liquid comprising from 20 to 99.9% liquid and from 80 to 0.1% of said hydrated lipidic lamellar phase, and
   (c) directly feeding said dispersion under a feeding pressure ranging between about 10,000 kPa and about 70,000 kPa into a passageway of small width defined between the walls of an orifice and the edges of an obturating element adjustably arranged in the section of said orifice, against the flow of said dispersion,
   thereby encapsulating said liquid within lipidic lamellar particles of said lipidic lamellar phase by entrapping a part of said aqueous liquid within said lipidic lamellar particles and forming a suspension in homogenized form of said encapsulated particles in the remaining liquid, thus achieving a high rate of encapsulation of said aqueous liquid in said lipidic lamellar particles.

4. A method for obtaining a homogenized suspension of hydrated lipidic lamellar phases entrapping a liquid, comprising the successive steps of:
   (a) providing a liquid comprising a biologically active product,
   (b) dispersing in said liquid, a lipidic phase or a lipidic lamellar phase containing at least one amphiphilic lipid, thereby obtaining a dispersion of said lipidic phase or lipidic lamellar phase in said liquid, and
   (c) directly feeding said dispersion under a feeding pressure ranging between about 10,000 kPa and about 70,000 kPa into a passageway of small width defined between the walls of an orifice and the edges of an obturating element adjustably arranged in the section of said orifice, against the flow of said dispersion, thereby encapsulating said liquid within lipidic lamellar particles of said lipidic lamellar phase by entrapping a part of said liquid comprising said biologically active product within said lipidic lamellar particles and forming a suspension in homogenized form of said encapsulated particles in the remaining liquid, thus achieving a high rate of encapsulation of said liquid within said biologically active product within said lipidic lamellar particles.

5. A method for obtaining a homogenized suspension of hydrated lipidic lamellar phases entrapping a liquid, comprising the successive steps of:
(a) providing a liquid comprising a product which possesses organoleptic properties,
(b) dispersing in said liquid, a lipidic phase or a lipidic lamellar phase containing at least one amphiphilic lipid, thereby obtaining a dispersion of said lipidic phase or lipidic lamellar phase in said liquid, and
(c) directly feeding said dispersion under a feeding pressure ranging between about 10,000 kPa and about 70,000 kPa into a passageway of small width defined between the walls of an orifice and the edges of an obturating element adjustably arranged in the section of said orifice, against the flow of said dispersion, thereby encapsulating said liquid within lipidic lamellar particles of said lipidic lamellar phase by entrapping a part of said liquid with said product which possesses organoleptic properties within said lipidic lamellar particles and forming a suspension in homogenized form of said encapsulated particles in the remaining liquid, thus achieving a high rate of encapsulation of said liquid comprising said product which possesses organoleptic properties within said lipidic lamellar particles.

6. The method of claim 3, wherein said feeding pressure ranges between about 10,000 kPa and about 40,000 kPa.

7. The method of claim 3, wherein said feeding pressure is about 30,000 kPa.

8. The method of claim 3, wherein said lipidic lamellar phase is a weakly hydrated lipidic lamellar phase with a content of lipidic phase ranging between about 50% and 80%.

9. The method of claim 3, wherein several successive passages of said dispersion through said passageway are performed.

10. The method of claim 3, wherein said dispersion to be homogenized is pre-fed under pressure into a device ensuring the feeding of said dispersion under pressure into said passageway.

11. The method of claim 10, wherein said pre-feeding of said dispersion under pressure is performed in an inert or a non-oxidizing atmosphere.

12. The method of claim 3, wherein said liquid of said dispersion is a physiological aqueous solution of sodium chloride or of d-glucose.

13. A suspension of hydrated lipidic lamellar phases entrapping a liquid, in said liquid, obtained by dispersing in an appropriate liquid a lipidic phase or lipidic lamellar phase containing at least one amphiphilic lipid, thereby obtaining a dispersion of said lipidic phase or lipidic lamellar phase in said liquid, and then homogenizing said dispersion by directly feeding the same under a feeding pressure ranging between about 10,000 kPa and about 70,000 kPa into a passageway of small width defined between the walls of an orifice and the edges of an obturating element adjustably arranged in the section of said orifice, against the flow of said dispersion, thereby encapsulating said liquid within lipidic lamellar particles of said lipidic lamellar phase by entrapping a part of said liquid within said lipidic lamellar particles and forming a suspension in homogenized form of said encapsulated particles in the remaining liquid, thus achieving a high rate of encapsulation of said aqueous liquid within said lipidic lamellar particles, the size of said lipidic lamellar particles ranging between 30 and 150 nanometers.

14. The suspension of claim 13, sterilized by way of sterilizing filtration.

15. The method of claim 1, additionally comprising dispersing at least one hydrophobic constituent in said liquid in step (b).

16. The method of claim 1, wherein said amphiphilic lipid is lecithin.

17. The method of claim 2, additionally comprising dispersing at least one hydrophobic constituent in said liquid in step (b).

18. The method of claim 2, wherein said amphiphilic lipid is lecithin.

19. The method of claim 3, additionally comprising dispersing at least one hydrophobic constituent in said liquid in step (b).

20. The method of claim 3, wherein said amphiphilic lipid is lecithin.

21. The method of claim 4, additionally comprising dispersing at least one hydrophobic constituent in said liquid in step (b).

22. The method of claim 4, wherein said amphiphilic lipid is lecithin.

23. The method of claim 5, additionally comprising dispersing at least one hydrophobic constituent in said liquid in step (b).

24. The method of claim 5, wherein said amphiphilic lipid is lecithin.

25. The method of claim 9, additionally comprising cooling said dispersion before each such passage.

26. The suspension of claim 13, additionally comprising at least one hydrophobic constituent in said lipidic phase or lipidic lamellar phase.

27. The suspension of claim 13, wherein said amphiphilic lipid is lecithin.

28. The suspension of claim 13, wherein the size of said lipidic lamellar particles is about 100 nanometers.

29. The suspension of claim 14, which is sterilized at about room temperature.

* * * * *